United States Patent [19]
Box et al.

[11] Patent Number: 5,906,918
[45] Date of Patent: May 25, 1999

[54] COMPOSITIONS AND METHODS FOR MEASUREMENT OF OXIDATIVE DNA DAMAGE

[75] Inventors: Harold C. Box, Williamsville; Alexander E. Maccubbin, Kenmore; Edwin E. Budzinski, West Seneca; Herbert Iijima, Williamsville, all of N.Y.

[73] Assignee: Health Research Inc., Buffalo, N.Y.

[21] Appl. No.: 08/797,758

[22] Filed: Feb. 7, 1997

[51] Int. Cl.[6] ............................. C12Q 1/68; C12P 19/34
[52] U.S. Cl. ................................. 435/6; 435/91.1
[58] Field of Search ............................. 435/91.1, 173.2, 435/183, 4, 6; 536/23.1, 24.3, 26.6, 25.3, 25.31, 25.32, 25.4, 25.41, 25.6–25.5; 204/182.8

[56] References Cited

U.S. PATENT DOCUMENTS 5,140,043   8/1992   Darr et al. ............................. 514/474
5,552,285   9/1996   Frenkel ................................. 435/7.1

OTHER PUBLICATIONS

"The Photocreactivity of Pyrimidine–Purine Sequences in Some Deoxydinucleoside Monophosphates and Alternating DNA Copolymers," Kumar, S and Davies, R.J.H. *Photochemistry and Photobiology* vol. 45 No. 5 pp. 571–579, May 1987.

Weinfeld et al. "Influence of nucleic acid base aromaticity on substrate reactivity with enzymes acting on single stranded DNA", Nucleic Acids Res. vol. 21, pp. 621–626, 1993.

Maccubbin et al. "32–P Postlabeling assay for free radical–induced DNA damage:the formamido remnant of thymine", Free Rad. Res. Comm. vol. 18, pp. 17–28, 1993.

Itakura et al. "Chemical Synthesis and Sequence Studies of Deoxyribooligonucleotides which Constitute the Duplex Sequence of the Lactose Operator of Escherichia coli", J. of Biol. Chem. vol. 259, pp. 4592–4600, 1976.

Ide et al. "Thymine glycols and urea residues in M13 DNA constitute replicative blocks in vitro", Nucleic Acids Research, vol. 13, pp. 8035–8052, 1985.

Maccubbin et al., P–Postlabeling Assay for Free Radical–Induced DNA Damage: The Formamido Remnant of Thymine, Sep. 13, 1992, "Free Rad. Res. Comms.", vol. 18, No. 1, pp. 17–28.

*Primary Examiner*—Lisa Arthur
*Assistant Examiner*—Jehanne Souaya
*Attorney, Agent, or Firm*—Hodgson, Russ, Andrews, Woods & Goodyear, LLP

[57] ABSTRACT

A method is provided for detecting and quantitating a DNA base modification in a sample of DNA, wherein the method involves an endonuclease digestion step, a labeling step, and a chromatographic separation step. Utilized in the method are compositions including a carrier for the DNA base modification, an internal standard, and a carrier for the internal standard. Also provided are methods for synthesizing the compositions, and kits containing the compositions.

30 Claims, 7 Drawing Sheets

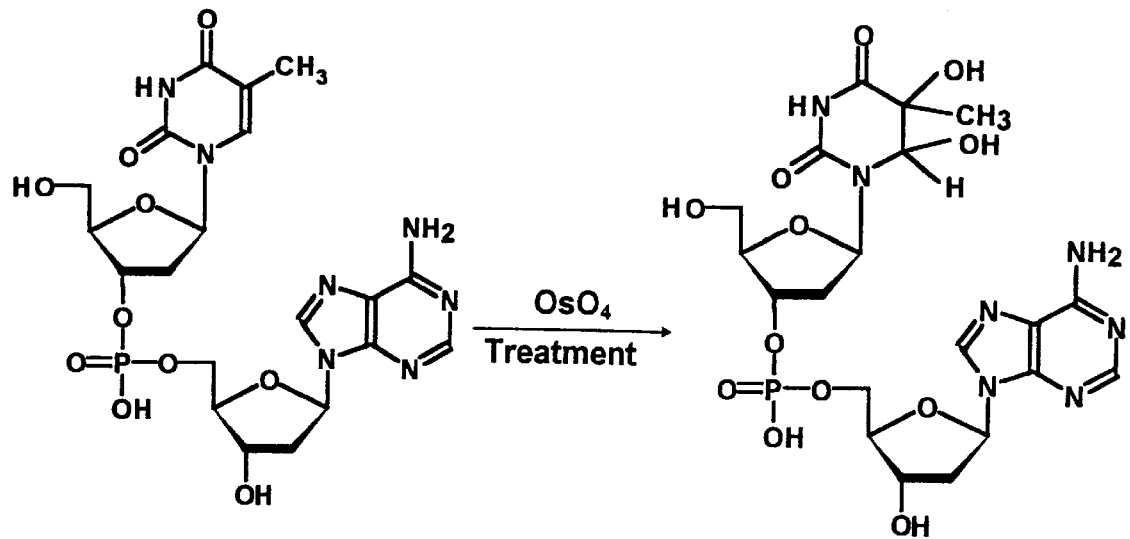
FIG. 4A
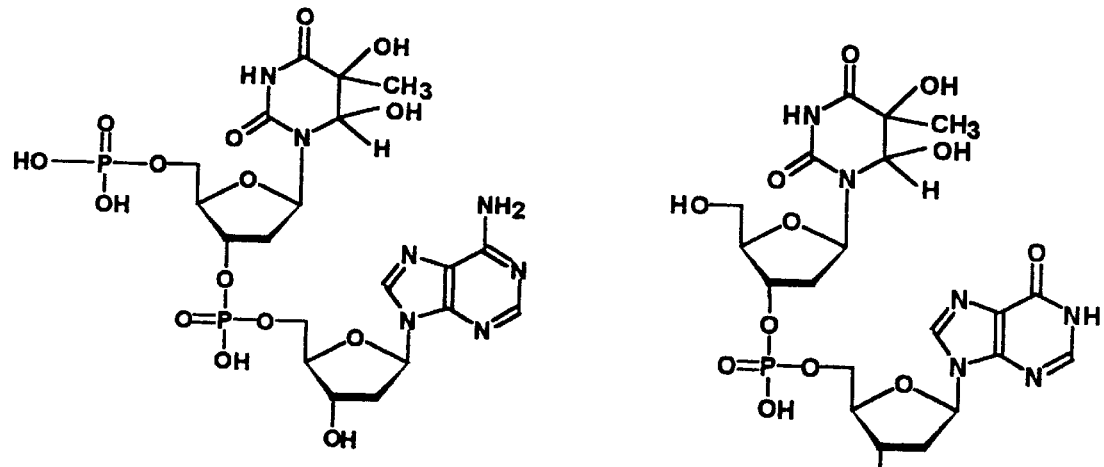
FIG. 4B
FIG. 4C
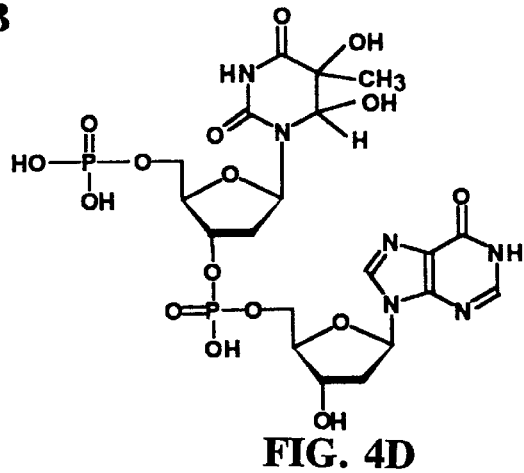
FIG. 4D

COMPOSITIONS AND METHODS FOR MEASUREMENT OF OXIDATIVE DNA DAMAGE

This invention was made with government support under grant numbers CA46838, and AG11965 awarded by the National Institutes of Health. The government has certain rights in this invention.

FIELD OF THE INVENTION

The present invention relates to novel compositions and methods for detection of DNA damage. More particularly, the present invention relates to genetic testing with novel compositions in providing methods for identifying and quantitating oxidative damage to DNA.

BACKGROUND OF THE INVENTION

Free radicals, or reactive oxygen species, are generated in vivo by a variety of mechanisms including oxidative stress, redox cycling, and ionizing radiation. For example, hydrogen peroxide ($H_2O_2$) can be generated endogenously by a number of cellular processes. $H_2O_2$, once in the nucleus of a cell, can lead to formation of hydroxyl radicals which then cause site-specific damage to DNA such as oxidation of DNA bases. Depending on the mechanism which generates the free radicals, free-radical induced oxidative DNA base modifications include 8-hydroxy-guanine, thymine glycol, formamido remnant, dihydrothymine, 5-hydroxymethl uracil, and 5-hydroxy-5-methylhydantoin.

Oxidative DNA damage has been associated with several pathological conditions including Alzheimer's disease (Mecocci et al., 1994, *Ann. Neurolog.* 36:747–751; Prashad et al., 1996, *Proc. Natl. Acad. Sci. USA* 93:5146–50), radiation exposure (Wilson et al., 1992, *Cancer Res.* 48:2156–2162), ischemic damage and stroke (1996, NIH Guide 25), metal toxicity (Carmichael et al., 1995, *Mutat. Research* 326:235–43), breast cancer (Djuric et al., 1996, *Cancer* 77:691–6), carcinogenesis (Ames et al., 1995, *Proc. Natl. Acad. Sci. USA* 92:5258–65), and other inflammatory processes. For example, the process of carcinogenesis is believed to require. multiple genetic and/or epigenetic events which affect patterns of expression, or result in mutational alteration, of genes. Molecular mechanisms, including oxidative DNA damage and alteration of a cell's ability to repair damaged DNA, may lead to the development of genomic instability. Genomic instability is believed to occur in an early step in the process of carcinogenesis.

There is a need for sensitive assays for specific lesions resulting from oxidative DNA damage. For example, it is known to those skilled in the art that exposure of an individual to UV irradiation, ionizing radiation, or certain chemo-therapeutic agents, can result in oxidative DNA damage. Thus, there is a need for means, such as the methods and compositions according to the present invention, which are clinically useful to assess exposure to chemotherapy or radiation therapy. Additionally, for individuals at high risk of a pathological condition associated with oxidative DNA damage, it may be useful to monitor the levels of specific DNA base modifications resulting from oxidative DNA damage prior to clinical onset of the condition. However, with the exception of thymine glycol which can be measured using an immunoassay (Hubbard-Smith et al., 1992, *Radiat. Res.* 130:160–5; U.S. Pat. No. 5,552,285) or by mass spectrometric analyses (Markey et al., 1993, *Ann. NY Acad. Sci.* 679:352–7), quantitation of each specific DNA base modification has been hindered by the lack of sensitivity of existing assays to detect biologically significant levels of each modification amongst the variety of base modifications that may be present.

SUMMARY OF THE INVENTION

It appears that in certain environmental or pathological conditions, free radical-induced oxidative DNA damage forms at a rate exceeding the ability of endogenous DNA repair mechanisms. A predominate type of free radical-induced oxidative DNA damage comprises DNA base modification. More particularly, DNA base modifications useful in the methods, and as compositions, of the present invention include but are not limited to the formamido remnant, the dihydrothymine modification, and the thymine glycol modification.

The present invention is directed to methods, compositions, and kits, to facilitate accurate measurement of DNA base modifications in cells and tissues. Measurements of a specific DNA base modification are carried out at the dimer level. In one embodiment, the method of the present invention comprises a nuclease digestion step, a labeling step, and a chromatographic separation step. Certain DNA base modifications prevent or significantly inhibit the hydrolysis of the neighboring phosphodiester bond by an endonuclease which hydrolyzes single stranded DNA. Thus, a sample of DNA to be assayed for the presence of DNA base modifications is digested with the endonuclease; and then with a phosphatase which dephosphorylates terminal phosphate groups. Dinucleoside monophosphates (nuclease resistant dimers) containing the DNA base modification are then chromatographically separated from digested monomers. A labeling step involves enzymatically labeling the dephosphorylated dinucleoside monophosphates with a phosphate having incorporated a detectable label (e.g., by using polynucleotide kinase together with $^{32}P$-ATP). Following labeling, and to reduce the background level radioactivity, the labeled dinucleoside monophosphates are separated from the unincorporated label by a simple filtration step. A cold phosphorylated carrier, chemically very similar or identical (such that the carrier co-chromatographs with the modified dinucleoside monophosphate) to the dinucleoside monophosphate containing the specific DNA modification sought to be quantitated, is then added to allow for identification of the specific DNA modification by the subsequent chromatographic separation step. An internal standard, and carrier therefor, is included in the method as an internal measure of the efficiency of phosphorylation (the step of incorporating a detectable label) and isolation, thereby allowing for accurate and sensitive quantitation.

In another embodiment of the method of the present invention, endonuclease-mediated partial hydrolysates of the sample DNA are used in the instance where the DNA base modification retards, but does not entirely prevent hydrolysis of the phosphoester bond 3' to the DNA base modification. Such DNA base modifications useful in the methods, and as compositions, of the present invention include but are not limited to 5-hydroxy-5-methylhydantoin, the 5-hydroxymethyluracil, and the 8-hydroxyguanine.

The present invention is also directed to methods for chemically synthesizing carriers and internal standards to facilitate accurate measurement of oxidative DNA damage in cells and tissues. In that regard, an additional object of the present invention is to provide kits comprising compositions selected from the group consisting of chemically synthesized carriers, internal standards, ancillary reagents, and filters used, in either the nuclease digestion step or labeling step or chromatographic separation step of the method of the present invention to detect and quantitate DNA base modifications in a sample of DNA.

Other objects, features, and advantages of the present invention will become apparent from the following drawings and detailed description.

BRIEF DESCRIPTION OF THE DRAWINGS

FIG. 4A illustrates a step in the chemical synthesis of the carrier shown in FIG. 4B.

FIG. 4B is a chemical structure of a carrier for detecting and quantitating a thymine glycol modification.

FIG. 4C is a chemical structure of a internal standard for detecting and quantitating a thymine glycol modification.

FIG. 4D is a chemical structure of a carrier for the internal standard shown in FIG. 4C.

DETAILED DESCRIPTION OF THE INVENTION

Definitions

Figure 1A:
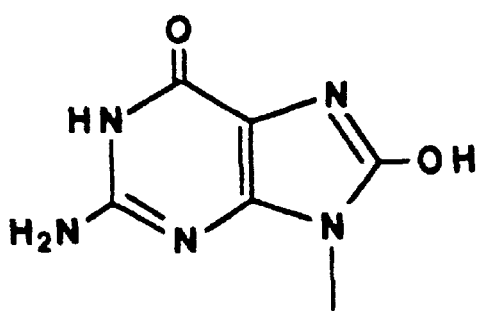
FIG. 1A is a representation of the DNA base modification 8-hydroxyguanine.
Figure 1F:
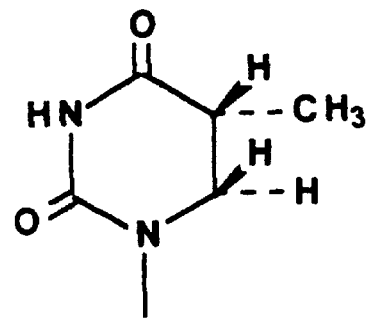
FIG. 1F and FIG. 1G are representations of the DNA base modifications dihydrothymine.
Figure 1B:
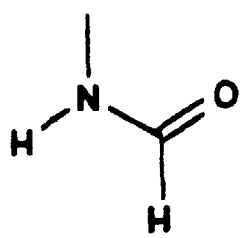
FIG. 1B is a representation of the formamido remnant of pyrimidines.
Figure 1G:
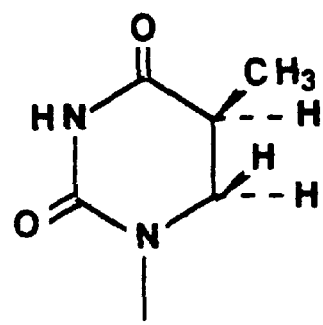
Figure 1C:
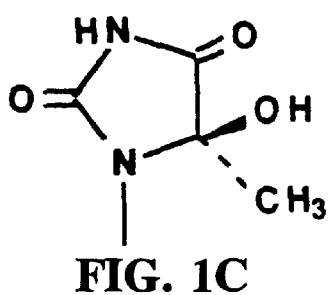
FIG. 1C and FIG. 1D are representations of the DNA base modifications 5-hydroxy-5-methylhydantoin.
Figure 1H:
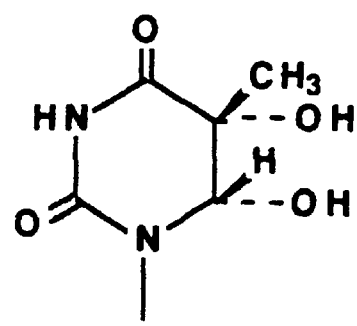
FIG. 1H and FIG. 1I are representations of the DNA base modification thymine glycol.
Figure 1D:
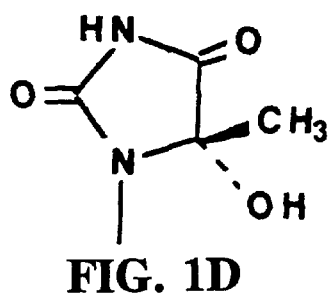
Figure 1I:
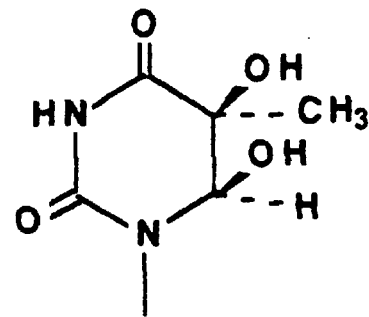
Figure 1E:
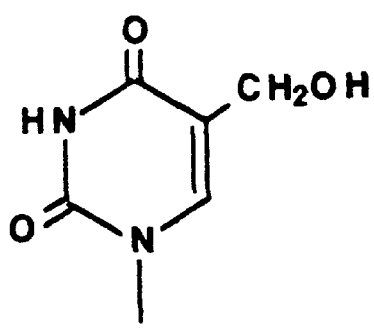
FIG. 1E is a representation of the DNA base modification 5-hydroxymethyluracil.

By the term "DNA base modifications" is meant, for the purposes of the specification and claims, to refer to DNA bases modified as a result of oxidative stress. DNA bases are known to those skilled in the art to include purines adenine and guanine, and pyrimidines thymine (5-methyl uracil), cytosine and 5-methyl cytosine. DNA bases modifications resulting from oxidative stress, are known to include, but are not limited to 8-hydroxyguanine (FIG. 1A), formamido remnant of pyrimidines (FIG. 1B), 5-hydroxy-5-methylhydantoin (FIGS. 1C and 1D), 5-hydroxymethyluracil (oxidized thymine; FIG. 1E), 5,6-dihydrothymine (hereinafter referred to as dihydrothymine; FIGS. 1F and 1G), and 5,6-dihydroxy-5,6-dihydrothymine (hereinafter referred to as thymine glycol; FIGS. 1H and 1I). Many other DNA bases modifications resulting from oxidative stress have been identified and are known to those skilled in the art (Teoule, 1987, *J. Radiation Biol.* 51:573–89; Teebor et al., 1988, *J. Radiation Biol.* 54:131–50; hereby incorporated by reference).

By the terms "detectable label" or "label" is meant, for the purposes of the specification and claims, to refer to an isotopic molecule which is incorporated indirectly or directly onto a terminal phosphate group. For example, the label molecule facilitates the detection of the DNA molecules having incorporated the label. To incorporate a label into a DNA molecule, the DNA molecule is end-labeled with the aid of an enzyme such as polynucleotide kinase (See for example, *Molecular Cloning*, a laboratory manual: editors Sambrook, Fritsch, Maniatis; Cold Spring Harbor Laboratory Press, 1989). While use of $\gamma^{32}$P-ATP is exemplified in particular detail in the following illustrative embodiments, other isotopic P-ATP labels could be used according to the method of the present invention for detection and quantitation using standard methods known in the art.

By the term "cold phosphorylated" is meant, for the purposes of the specification and claims, to refer to phosphorylation of a dephosphorylated DNA molecule (or dinucleoside monophosphate) using phosphate (e.g. in the form of ATP) without an isotopic label.

By the term "chromatographic separation" is meant, for the purposes of the specification and claims, to refer to solid phase (e.g., thin layer chromatography, TLC) or liquid phase (e.g., high pressure liquid chromatography) processes known in the art for separating molecules by size and/or other molecular characteristics.

By the term "endonuclease" is meant, for the purposes of the specification and claims, to refer to an enzyme which specifically hydrolyzes single stranded nucleic acid molecules such as single stranded DNA. Such enzymes are known to those skilled in the art to include, but not limited to, nuclease P1 and nuclease S1.

By the term "labeling step"is meant, for the purposes of the specification and claims, to refer to the process of adding a detectable label to molecules of interest, and a subsequent initial simple filtration to remove unbound label.

While the invention has been generally described above, the invention will be described in more detail in the following examples which are provided by way of illustration, but not limitation.

EXAMPLE 1

A $^{32}$P-postlabeling assay has been developed for detection of the formamido remnant d(T*pA) as described previously (Maccubbin et al., 1993, *Free Rad. Res. Commun.* 18:17–28; herein incorporated by reference). This assay for detecting the formamido remnant uses some of the same basic principles of the method according to the present invention. The formamido remnant d(T*pA) (where "d" represents "dimer or dinucleoside monophosphate"; T is thymine which is modified; "*" denotes the modification, "p" represents the phosphate linking T and A, wherein A is adenosine) was detected in the following manner. DNA, which was previously irradiated, was analyzed for the formamido remnant. A model dimer d(TpA) was also irradiated to generate the dimer d(T*pA) which was purified as described previously (Belfi et al., 1986, *Radiat. Res.* 106:17–30). The purified d(T*pA) was used as a standard for optimizing the postlabeling conditions, and was also used to synthesize the carrier used in the detection process. The DNA (100 µg) was digested with endonuclease (nuclease P1, 0.48 µg) in a 1 ml solution containing 1.44 µl of 30 mM $ZnCl_2$ and 240 µl of 0.25M sodium acetate (pH 5.0) at 37° C. for 3 hours. Dephosphorylation of the endonuclease digested DNA was performed by adding 3.3 µl of a solution containing 100 mU per µl of prostatic acid phosphatase. The reactions were terminated by the addition of 23.3 µl of 0.1M 2[N-cyclohexylamino]-ethane sulfonic acid (CHES) buffer, pH 9.5. Each enzyme treatment was repeated to ensure digestion.

Digested dephosphorylated DNA was then applied to a 3µC18 reverse phase HPLC column and eluted at 0.2 ml per minute for 30 minutes with 0.1M ammonium acetate, followed by a 60 minute 0–10% acetonitrile gradient in 0.1M ammonium acetate at a flow rate of 2 ml per minute followed by isocratic elution at 2 ml per minute with 10% acetonitrile in 0.1M ammonium acetate. A fraction containing the d(T*pA) dinucleoside monophosphate was collected and then desalted by HPLC using 1 M ammonium acetate with a 30 minute 0–50% methanol gradient.

The d(T*pA) dinucleoside monophosphate purified from the DNA digest was labeled with the detectable label, $^{32}$p, Polynucleotide kinase (10 units), $\gamma^{32}$P-ATP (50 µCi at typically 3000 Ci/mmol) unlabeled ATP (final concentration of 60 µM), and reaction buffer (200 mM Bicine, pH 9.5, 100 mM $MgCl_2$, 100 mM dithiothrietol, 10 mM spermidine) was mixed with the dinucleoside monophosphate (2.0 optical density units) and incubated for 45 minutes at 37° C. The labeling reaction was terminated by the adding apyrase and then incubating for 30 minutes at 37° C. Nonradioactive synthesized dimer pd(T*pA) (formed by cold-phosphorylating the dimer d(T*pA)) was added as a carrier to the labeled d(T*pA) dinucleoside monophosphate and was then purified by chromatography using a C18 solid phase extraction column pre-equilibrated with 50 mM triethanolamine acetate, pH 7.0 (TEAA); the column was washed to remove free inorganic phosphate; and the labeled d(T*pA) dinucleoside monophosphate and carrier was eluted with 50% acetonitrile in 50 mM TEAA buffer. Purified labeled d(T*A) dinucleoside monophosphate and carrier were dried, and redissolved in buffer. The mixture was then separated from background components by chromatographic separation (two-dimensional TLC).

The sample containing labeled d(T*pA) dinucleoside monophosphate and non-radioactive carrier pd(T*pA) dimer was spotted onto a TLC plate that had been pre-equilibrated with 0.225M ammonium formate, pH 3.5. The non-radioactive carrier pd(T*pA) served as a marker for migration/elution in the chromatographic separation procedure. The plate was then developed from bottom to top with 2.25M ammonium formate, pH 3.5 followed by rinsing in distilled water and methanol, and then allowed to dry. The plate was then turned 90° C. and chromatographed to the top of the plate in the second dimension in 1M lithium chloride. The plate was then dried, and label was detected by autoradiography. The synthesized dimer acted as a carrier which serves to track and locate (e.g., by ultraviolet absorption 260 nm) the labeled formamido remnant by co-migration with the labeled formamido remnant during chromatographic separations. The spot on the TLC plate, as determined by autoradiography, which represented the d(T*pA) dinucleoside monophosphate from the original DNA sample was cut from the plate and radioactivity counted by liquid scintillation spectrometry. Based on the specific activity of the label ($^{32}$P-ATP) the amount of DNA in the original digest and the radioactivity in the spot, the level of the formamido remnant was calculated using the following formula:

$$\text{formamido remnant d(T*pA) in fmol/µg DNA} = [\text{amount of label measured/specific activity}]/\text{µg DNA digested;}$$

wherein the amount of label (eluted with the carrier) is measured in disintegrations per minute (dpm), and the specific activity is measured in dpm per fmol.

Using this method, the yield of formamido remnant d(T*pA) in the original sample of DNA was calculated to be 18 femtomoles per microgram of DNA per Gy (measure of radiation dose), or 1.8 formamido lesions d(T*pA) formed per $10^5$ thymine bases per Gy. A background level of 11 femtomoles per microgram was measured for d(T*pA).

In another embodiment, the sample containing labeled d(T*pA) dinucleoside monophosphate and non-radioactive pd(T*pA) dimer can be chromatographically separated from background components using HPLC in isolating a fraction for quantitating the yield of formamido remnant d(T*pA) in the original sample of DNA, followed by detecting and quantitating the amount of label.

The above-assay and assay components, while being an improvement in sensitivity over previous assays, still has several drawbacks which the compositions of the present invention specifically address. In the assay as described above, there are some variables which can affect the final quantitation. For example, the carrier used was constructed by irradiation of the dimer d(TpA) in forming d(T*pA). However, such method for producing the carrier is both inefficient and chaotic. Thus, there is a need for a method which can reliably and efficiently result in the production of a carrier for use in tracking and locating in a postlabeling assay the DNA base modification consisting of the formamido remnant.

Additionally, depending on such factors as the storage, age, and the variation associated with different lots of the product, the enzymatic activity of the polynucleotide kinase may vary. Such variation in enzymatic activity affects the degree of efficiency of phosphorylation with radiolabel of the dinucleoside monophosphate sought to be measured. Further, the postlabeling assay involves more than one chromatographic step in which some loss of product occurs. Each of these variables can affect the final quantitation of the dinucleoside monophosphate sought to be measured. Thus, there is a need for an internal standard ("positive control") which can be used to take into account such variables as the efficiency of labeling and possible loss of product during chromatographic separation in achieving an accurate quantitation of the DNA base modification. However, for the internal standard to be effective, it too would require a carrier which serves to track and locate (e.g., by natural fluorescence, or by ultraviolet absorption) the internal standard by co-migration with the internal standard during chromatographic separations.

EXAMPLE 2

Figure 2A:
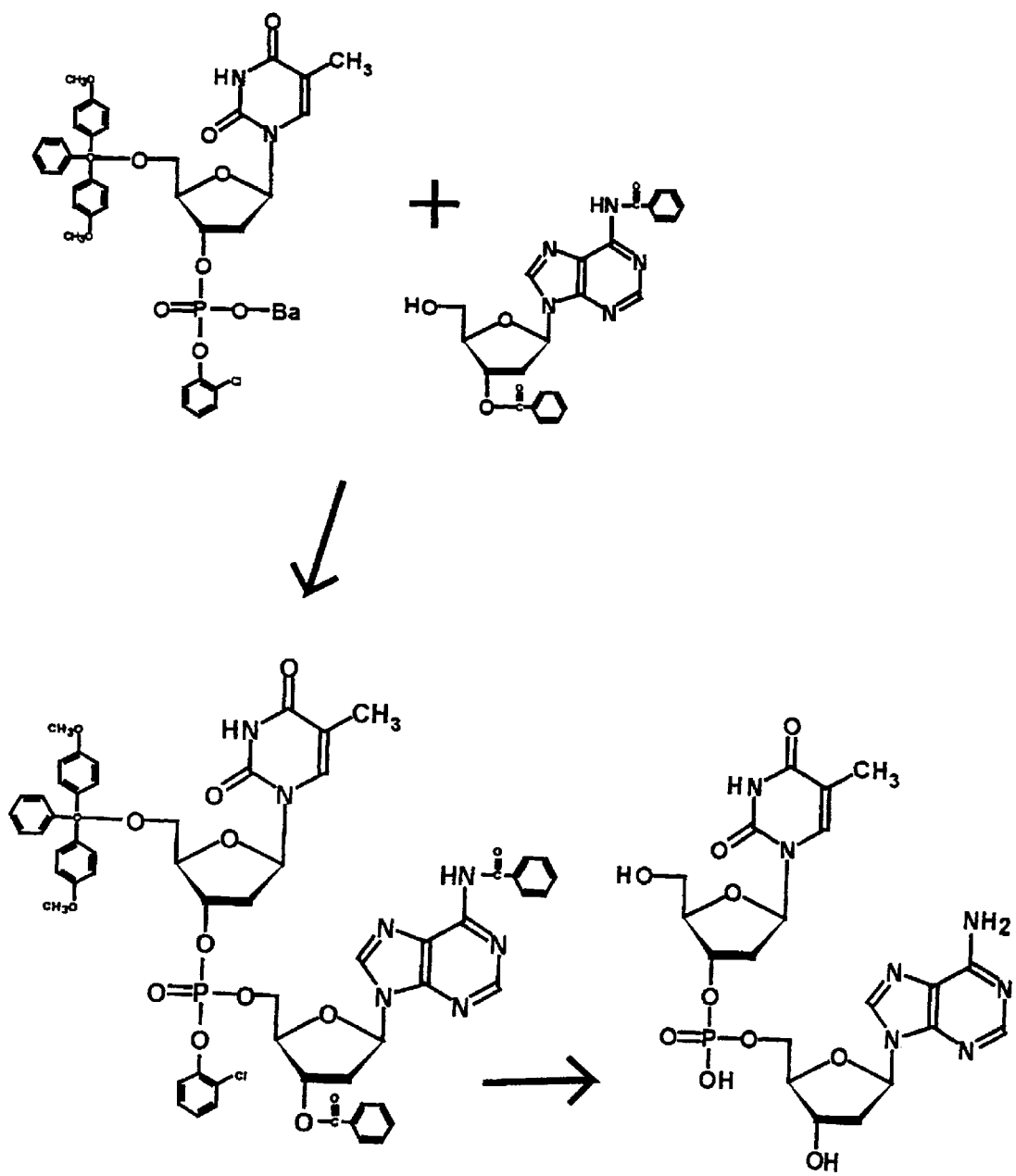
FIG. 2A illustrates the chemical synthesis of the dinucleoside monphosphate d(TpA) in bulk.

In this embodiment of the present invention, illustrated and provided are compositions for improving the efficiency and sensitivity of a postlabeling assay for detecting and quantitating the DNA base modification consisting of the formamido remnant d(T*pA). Also illustrated and provided in this embodiment are methods for reliably and efficiently producing the compositions according to the present invention. For the carrier for the formamido remnant d(T*pA), the initial step involves the chemical synthesis of the dinucleoside monophosphate d(TpA) in bulk. This initial step is illustrated in FIG. 2A. Briefly, d(TpA) was synthesized from 5'-O-dimethyoxytrityl-thymidine-3'-(o-chlorophenyl) phosphate barium salt and $N^6$-benzoyl-2'-deoxyadenosine using a phosphotriester method. In that regard, a stoichiometric mixture, or a mixture containing a slight excess of phosphorylated nucleotide, is dissolved in a suitable solvent such as anhydrous pyridine, and then is treated with an arylsulfonate such as triisopropylbenzenesulfonylimadizolate (in a three-fold excess of the phosphorylated nucleotide) or a three-fold excess of arylsufonylchlorite and a strong nucleophile such as methylimidazole in six fold excess, of the phosphorylated nucleotide. After condensation, the base labile protecting groups were removed by treatment with a strong base (e.g., ammonium chloride for 8 hours at 50° C.), and the acid labile protecting groups were removed by acid treatment (e.g., acetic acid for 1 hour, room temperature) to yield the dinucleoside monophosphate. Purification is achieved by chromatographic separation (HPLC) using a C18 reverse phase column and eluting with a 0%–10% linear gradient of acetonitrile/0.1M ammonium acetate buffer, pH 7.0 at a 3.0 ml/minute flow rate.

Figure 2B:
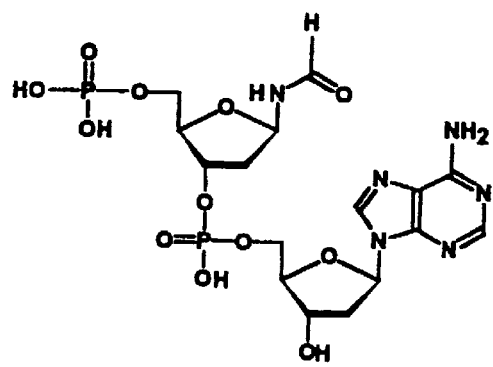
FIG. 2B is a chemical structure of a carrier for a formamido remnant d(T*pA).
Figure 2C:
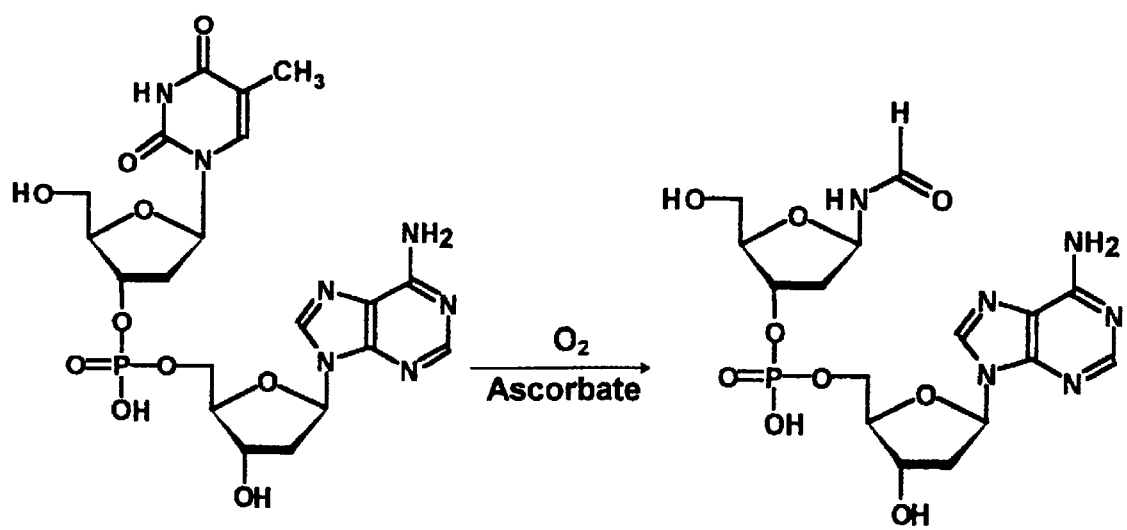
FIG. 2C illustrates a step in the chemical synthesis of the carrier shown in FIG. 2B.

From the d(TpA) produced is synthesized a carrier having the chemical structure illustrated in FIG. 2B, wherein the carrier is used for tracking and unequivocally locating in chromatographic separations the DNA base modification consisting of the formamido remnant d(T*pA). First, a dinucleoside monophosphate was synthesized by converting the normal 5' nucleoside of the d(TpA) to a formamido remnant d(T*pA) using a reaction summarized in FIG. 2C. Briefly, d(TpA) and ascorbic acid (each at a concentration of 1 mg/ml) are initially dissolved in nitrogen-saturated phosphate buffer (0.1M $NaH_2PO_4$, pH 6.8). The mixture is then purged with oxygen and left under oxygen pressure at 6 psi at room temperature in the dark for three days. The formamido remnant d(T*pA) product is then isolated by HPLC using the conditions essentially as described above, and the structure is then verified by proton nuclear magnetic resonance (NMR) spectroscopy. The yield of the end product is approximately 5%. It is important to note that the dinucleoside monophosphate so produced, as shown in FIG. 2C, has a deoxyribose molecule to which a terminal phosphate group can be added at position 5. Thus, to complete the synthesis of the carrier, the dinucleoside monophosphate is phosphorylated, such as by using polynucleotide kinase and ATP, resulting in the carrier shown in FIG. 2B. The carrier can then be purified by chromatography on an HPLC reverse phase C18 column using the conditions described above. The carrier may be desalted by lyophilizing the product, and then chromatographing on an HPLC reverse phase C18 column using a 0% to 50% methanol/10 mM ammonium acetate elution gradient.

Figure 3A:
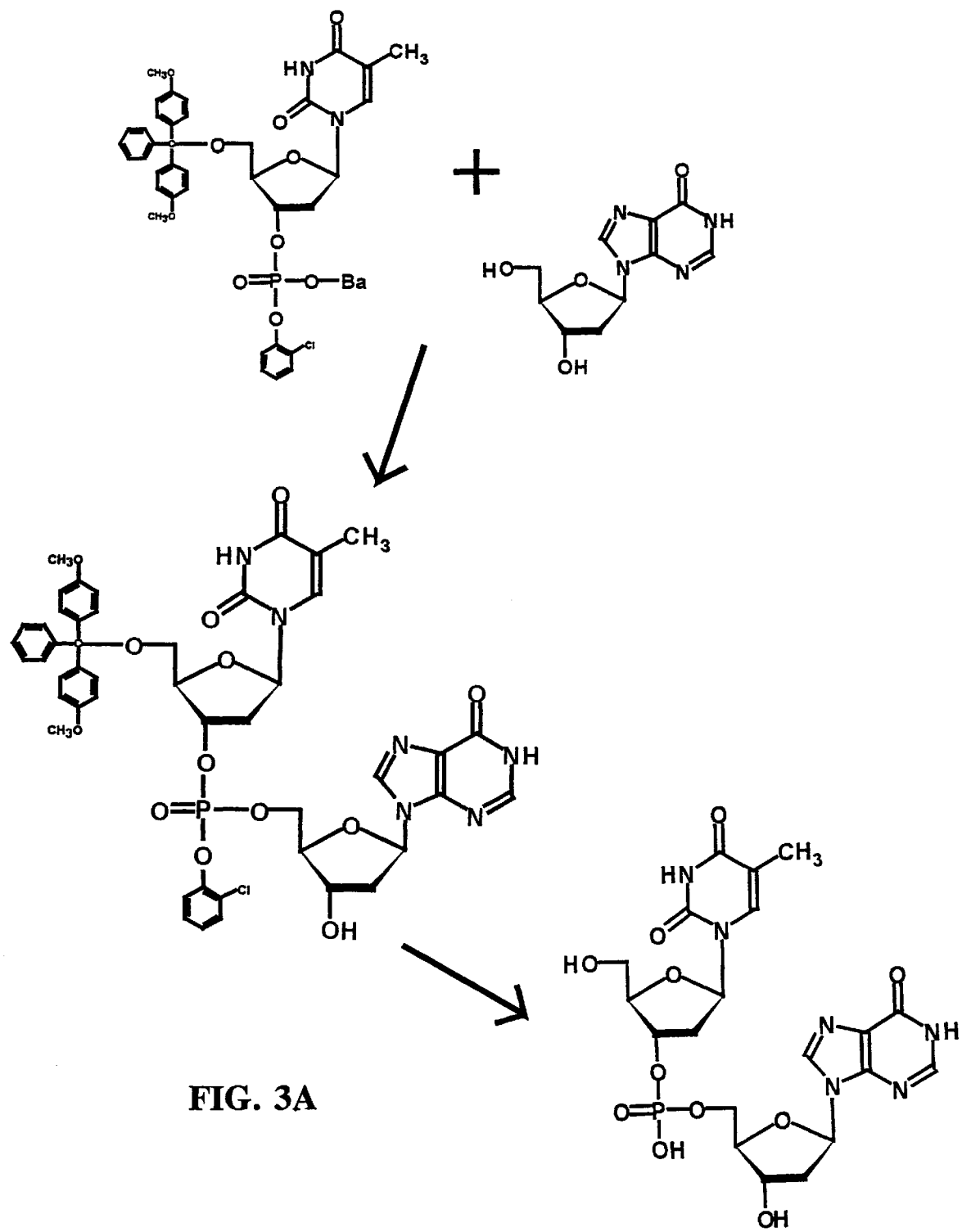
FIG. 3A illustrates the chemical synthesis of the dinucleoside monphosphate d(TpI) in bulk.

In another aspect of this embodiment, provided are an internal standard, and the carrier for the internal standard, for detecting and quantitating the DNA base modification consisting of the formamido remnant d(T*pA). For the internal standard, and the carrier for the internal standard, the initial step in each synthetic procedure involves the chemical synthesis of the dinucleoside monophosphate d(TpI) in bulk. This initial step is illustrated in FIG. 3A. Briefly, d(TpI) was synthesized from 5'-O-dimethyoxytrityl-thymidine-3'-(o-chlorophenyl) phosphate barium salt and 2'-deoxyinosine using a phosphotriester method using the same reaction conditions as described above. After condensation, the protection groups were removed by treatment, as described above for the synthesis of d(TpA), to yield the dinucleoside monophosphate. Purification is achieved by chromatographic separation (HPLC) using a C18 reverse phase column as described above for purification of d(TpA).

Figure 3B:
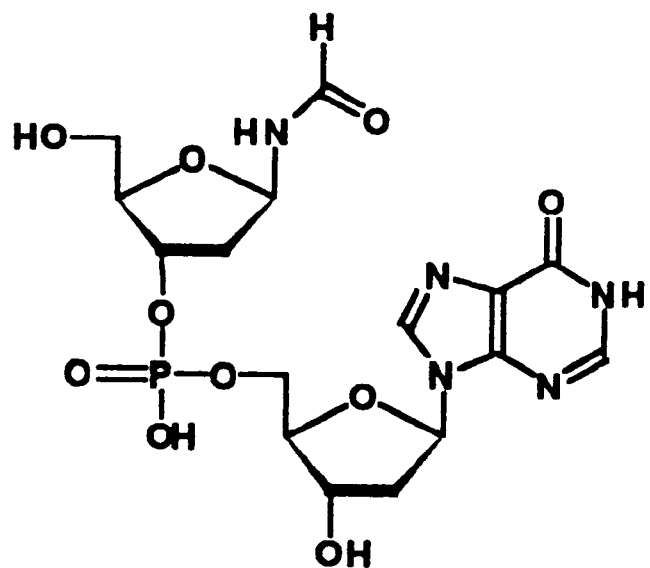
FIG. 3B is a chemical structure of a internal standard for detecting and quantitating a formamido remnant d(T*pA).

From the d(TpI) was synthesized an internal standard of the chemical structure shown in FIG. 3B. The internal standard was synthesized by incubating d(TpI) and ascorbic acid in an oxygenated environment using the conditions and subsequent purification by chromatography as essentially described above for producing the formamido remnant d(T*pA). It is important to note that the internal standard, as shown in FIG. 3B, has a deoxyribose molecule to which a terminal phosphate group can be added at position 5'. In one aspect of this embodiment, the internal standard is labeled using a detectable label such as $\gamma^{32}p$, by using polynucleotide kinase and $\gamma^{32}P$-ATP. Thus, in addition to using methods illustrated in Example 1 herein, a known amount of the internal standard can be labeled in the same reaction in which the d(T*pA) dinucleoside monophosphate purified from the DNA digest is labeled, and is present throughout the various steps of the assay. Thus, the internal standard provides a means by which variables, such as the efficiency of labeling and possible loss of product during chromatographic separation, can be taken into account in achieving an accurate quantitation of the DNA base modification.

Figure 3C:
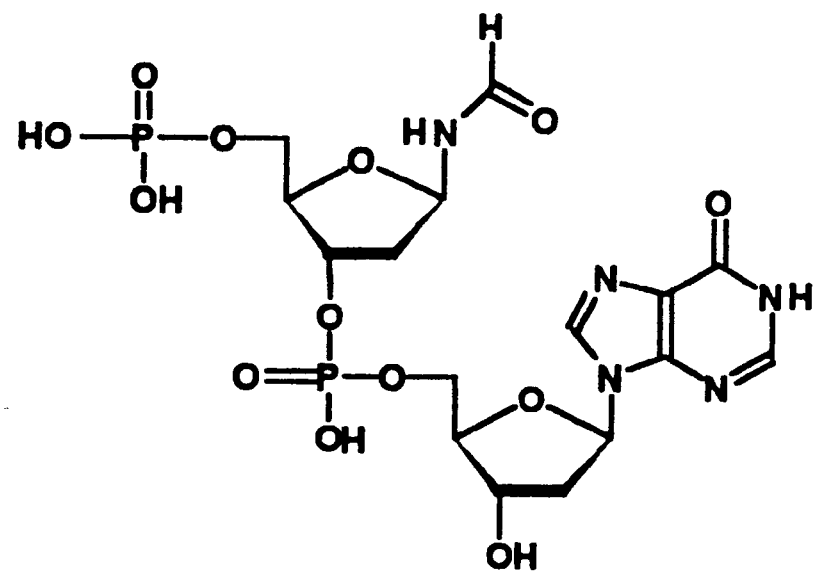
FIG. 3C is a chemical structure of a carrier for the internal standard shown in FIG. 3B.

In another aspect of this embodiment, a carrier having the chemical structure illustrated in FIG. 3C is synthesized from the internal standard by cold-phosphorylating the internal standard. Thus, using methods illustrated in Example 1 herein, polynucleotide kinase and ATP can be used to phosphorylate the internal standard in constructing a carrier for the internal standard, wherein the carrier is used to track and unequivocally locate (e.g., by natural fluorescence, or by ultraviolet absorption) the internal standard by co-migration with the internal standard during chromatographic separations.

In an additional aspect of this embodiment according to the present invention, provided is a kit for a method for detecting and quantitating the formamido remnant d(T*pA) in a DNA sample, wherein the kit comprises components selected from the group consisting of a chemically synthesized carrier for the formamido remnant, an internal standard, a carrier for the internal standard, ancillary reagents used in the nuclease digestion step (e.g., endonuclease, buffer used for the endonuclease digestion), ancillary reagents used in postlabeling step (e.g., phosphatase, buffer used for phosphatase, polynucleotide kinase, buffer for polynucleotide kinase, and ATP, and disposable filters), and a combination thereof.

EXAMPLE 3

Endonuclease digestion was found particularly suitable when employed as a step in a postlabeling assay for detecting and quantitating the DNA base modification comprising the formamido remnant d(T*pA) (Maccubbin et al., 1993, supra). The assay depended upon the discovery that endonucleases, such as nuclease P1, do not hydrolyze the phosphoester bond 3' to a nucleoside bearing a formamido remnant such as d(T*pA). Because of the resistance of this type of DNA base modification to endonuclease digestion, the bulk of the DNA digest is in the form of nucleoside monomers which are not acceptable substrates for the phosphorylation step. However, after endonuclease digestion, the formamido remnant such as d (T*pA) is in a modified dimer form, a dinucleoside monophosphate, which can be selectively labeled with a detectable label (e.g., using polynucleotide kinase and $\gamma^{32}P$-ATP).

It is known that the efficiency of endonuclease digestion depends largely on the nature of the substrate. In other words, at the time of the invention, while it was shown that endonuclease is effectively prevented from hydrolyzing the phosphoester bond 3' to a nucleoside bearing a formamido remnant d(T*pA), what was not known was the susceptibility or resistance of other DNA base modifications to endonuclease digestion. Thus, in this example, measurements were performed to determine the susceptibility/ resistance of DNA base modifications, other than the formamido remnant d(T*pA), to endonuclease digestion. The propensity of the endonuclease to hydrolyze DNA in a manner that renders a DNA base modification as modified dinucleoside monophosphates is information important to determine whether a method comprising a nuclease digestion step, a labeling step, and a chromatographic separation step may be used to detect and quantitate DNA base modifications, other than the formamido remnant d(T*pA).

The endonuclease turnover rate was measured in terms of the number of substrate molecules hydrolyzed per minute per molecule of enzyme. The substrates were modified dinucleoside monophosphates comprising the DNA base modifications illustrated in FIG. 1. The respective unmodified dinucleoside monophosphates were purchased commercially, with the exceptions of d(GpG), d(GpC), d(GpA), and d(GpT) which were prepared using methods previously described (Paul et al., 1988, *Int. J. Radiat. Biol.* 54:403–415). A solution of each the unmodified dinucleoside monophosphates was X-irradiated, and the corresponding modified dinucleoside monophosphate was isolated by reverse-phase HPLC (see, e.g., Schroder et al., 1995, *Int. J. Radiat. Biol.* 68:509–23; and Box et al., 1995, In *Radiation Damage in DNA*, eds. Fuciarelli and Zimbrick, publs. Battelle Press). The one exception to producing modified dinucleoside monophosphates was the production of the DNA base modification thymine glycol. Modified dinucleoside monophosphates bearing the thymine glycol modification were prepared by treating dTpA with osmium tetroxide (see, e.g., Belfi et al., 1986, supra). The DNA base modifications were identified using proton nuclear magnetic resonance spectroscopy (see, e.g., Schroder et al., 1995, *Int. J. Radiat. Biol.* 68:509–23).

Concentrations of the modified dinucleoside monophosphates were determined spectrophotometrically at 260 nm. The rates of hydrolysis for the modified dinucleoside monophosphates by endonuclease were obtained from measurements of equimolar amounts of the substrate modified dinucleoside monophosphate (6 nmol) in 100 µl of 60 mM sodium acetate buffer (pH 5.3, containing 42 µmol zinc chloride). Hydrolysis was initiated by the addition of the endonuclease (50 ng of nuclease P1 in 2 µl buffer) and the reactants were incubated in a 37° C. water bath. At varying times, hydrolysis was terminated by the addition of 15 µl of 1M Tris, and rapid freezing in a liquid nitrogen bath. The products of digestion were analyzed by injecting the digest onto a C-18 reverse phase HPLC column, with elution using a 5%–53% linear gradient of $CH_3CN$/0.1M ammonium acetate buffer, pH 7.0 at a 1.0 ml/minute flow rate. Moles of protein were calculated from the weight of the material and the known molecular weights for the constituents. The results of the measurement of the endonuclease turnover rates (R, as measured in terms of molecules hydrolyzed per minute per molecule of enzyme) for each of the modified dinucleoside monophosphates tested is illustrated in Table 1.

TABLE 1

| dNpN | DNA base modification | R |
|---|---|---|
| d(T*pA) | 5-hydroxy-5-methylhydantoin | 118 |
| d(G*pC) | 8-hydroxyguanine | 96 |
| d(G*pT) | 8-hydroxyguanine | 87 |
| d(T*pA) | 5-hydroxymethyluracil | 78 |
| d(T*pA) | 5-hydroxy-5-methylhydantoin | 28 |
| d(T*pA) | dihydrothymine | 3.6 |
| d(T*pA) | dihydrothymine | 1.3 |
| d(T*pA) | thymine glycol | 0.30 |
| d(T*pA) | thymine glycol | 0.27 |
| d(T*pG) | formamido remnant | no hydrolysis detected |
| d(T*pA) | formamido remnant | no hydrolysis detected |
| d(T*pC) | formamido remnant | no hydrolysis detected |
| d(T*pT) | formamido remnant | no hydrolysis detected |
| d(T*pG*) | tandem base modification | no hydrolysis detected |

From the results in Table 1, it is clear that only certain DNA base modifications confer substantial resistance to endonuclease digestion. Such modified dinucleoside monophosphates are selected from the group consisting of thymine glycol, dihydrothymine, a tandem base modification comprising-d(T*pG*), and certain, but not all, formamido remnants. Thus, the previously described postlabeling assay for the formamido remnant d(T*pA) (Maccubbin et al., 1993, supra) is not predictive of whether DNA modifications other than formamido remnants would confer substantial resistance to endonuclease digestion thus reliably producing dinucleoside monophosphates which can be selectively labeled with a detectable label in a postlabeling assay.

Therefore, the following embodiments of the present invention are based on the findings illustrated in Table 1. There is provided a method comprising a nuclease digestion step, a labeling step, and a chromatographic separation step to detect and quantitate a DNA base modification in a sample of DNA, wherein the DNA base modification prevents or significantly inhibits the hydrolysis of the neighboring phosphodiester bond by an endonuclease, and wherein the DNA base modification is selected from the group consisting of thymine glycol, dihydrothymine, a tandem base modification d(T*pG*), and a formamido remnant (d(T*pG), d(T*pC), d(T*pA), or d(T*pT)). There is also provided a method comprising an endonuclease-mediated partial hydrolysis step, a labeling step, and a chromatographic separation step to detect and quantitate a DNA base modification in a sample of DNA, wherein the DNA base modification retards, but does not entirely prevent hydrolysis of the phosphoester bond by an endonuclease, and wherein the DNA base modification is selected from the group consisting of 5-hydroxy-5-methylhydantoin, 5-hydroxymethyluracil, and 8-hydroxyguanine.

EXAMPLE 4

In this embodiment of the present invention, illustrated and provided is a method comprising a nuclease digestion step, a labeling step, and a chromatographic separation step to detect and quantitate a DNA base modification in a sample of DNA, wherein the DNA base modification prevents or significantly inhibits the hydrolysis of the neighboring phosphodiester bond by an endonuclease, and wherein the DNA base modification is selected from the group consisting of thymine glycol, dihydrothymine, a tandem base modification d(T*pG*), and a formamido remnant (d(T*pG), d(T*pC), d (T*pA) or d(T*pT)). Also illustrated and provided in this embodiment are compositions for improving the efficiency and sensitivity of the method according to the present invention, and methods for reliably and efficiently producing the compositions according to the present invention.

Thymine Glycol

In one aspect of this embodiment, the DNA base modification to be detected and quantitated is thymine glycol. The thymine glycol modification (d(T*pA)) is a free radical-induced base modification in which the stable glycol product is produced in DNA in an oxic or anoxic environment. Using the methods essentially according to Example 1 herein and additional compositions described herein, a method of detecting and quantitating thymine glycol in a sample of DNA comprises a nuclease digestion step, a labeling step, and a chromatographic separation step. First, the sample of DNA to be assayed is digested with endonuclease, and dephosphorylated with acid phosphatase. As shown in Table 1, the thymine glycol DNA base modification prevents or significantly inhibits the hydrolysis of the neighboring phosphodiester bond by an endonuclease. Therefore, the bulk of the DNA digest is in the form of nucleoside monomers which are not acceptable substrates for the phosphorylation step, and the remainder is modified dinucleoside monophosphates containing the thymine glycol modification which can be selectively labeled with a detectable label. The digested dephosphorylated DNA is then chromatographed to separate the modified dinucleoside monophosphates containing the thymine glycol modification from the nucleoside monomers. From this step on in the method, it may be desirable to include an internal standard for the thymine glycol modification to assist in the accurate detection and quantitation of the thymine glycol modification present in the sample DNA. The modified dinucleoside monophosphates and the internal standard are then (in the same reaction mixture) enzymatically labeled with a detectable label, and together the labeled modified dinucleoside monophosphates and labeled internal standard (collectively referred to as "labeled products") are separated from the radioactive debris residual from labeling by a simple filtration procedure in reducing significantly the level of background radioactivity. To further purify the labeled products from background radioactivity, the labeled products are subjected to chromatographic separation (e.g., TLC or HPLC). In preparing the labeled products for chromatography, a carrier for the thymine glycol modification is added to track and unequivocally locate (e.g., by natural fluorescence, or by ultraviolet absorption) the labeled modified dinucleoside monophosphates comprising the thymine glycol modification during the chromatographic separation; and a carrier for the internal standard is added to track and unequivocally locate the labeled internal standard during the chromatographic separation. The amount of label for the labeled modified dinucleoside monophosphates comprising the thymine glycol modification, and the amount of label for the labeled internal standard can then be detected and measured. Using the internal standard as a reference, the moles of the thymine glycol modification can be quantitated from the measure of label. As described previously, the internal standard is necessary for the quantitation of the DNA base modification because of such variables as the efficiency of phosphorylation.

In continuing with this aspect of the embodiment of the present invention, illustrated and provided are compositions for improving the efficiency and sensitivity of the method according to the present invention for detecting and quantitating the DNA base modification comprising the thymine glycol modification. Also illustrated and provided in this embodiment are methods for reliably and efficiently producing the compositions according to the present invention. For the carrier for the thymine glycol modification, the initial step involves the chemical synthesis of the dinucleoside monophosphate d(TpA) in bulk, as was described above and as illustrated in FIG. 2A. FIG. 4A summarizes the synthesis of the carrier for the thymine glycol modification from d(TpA). The carrier for the thymine glycol modification is synthesized from d(TpA) by dissolving 3.3 mg of d(TpA) in 250 µl $H_2O$ heated to 55° C., then adding 300 µl of 4% $OsO_4$. The solution is then incubated for 10 minutes at 55° C., cooled on ice, and then extracted 8 times with ether (300 µl). Purification is accomplished by HPLC as described above. The conversion (total of both cis isomers) is typically 25%. The carrier, having the chemical structure as shown in FIG. 4B, is used for tracking and unequivocally locating in the method of the present invention for detecting and quantitating the DNA base modification comprising the thymine glycol modification. Also in this embodiment, provided are an internal standard, and the carrier for the internal standard, for detecting and quantitating the DNA base modification comprising the thymine glycol modification. For the internal standard, and the carrier for the internal standard, the initial step in the synthetic procedure involves the chemical synthesis of the dinucleoside monophosphate d(TpI) in bulk, as described above and as illustrated in FIG. 3A. From the d(TpI) was synthesized an internal standard for the thymine glycol modification. The internal standard was synthesized by incubating d(TpI) in 4% $OsO_4$, with subsequent purification by chromatography as essentially described above for producing the carrier for the thymine glycol modification d(T*pA). It is important to note that this internal standard, as illustrated in FIG. 4C, has a deoxyribose molecule to which a terminal phosphate group can be added at position 5'. In one aspect of this embodiment, the internal standard is labeled using a detectable label such as $\gamma^{32}p$, by using polynucleotide kinase and $\gamma^{32}$P-ATP. Thus, in addition to using methods illustrated in Example 1 herein, a known amount of internal standard can be labeled in the same reaction mixture in which the thymine glycol modified dinucleoside monophosphate purified from the DNA digest is labeled. The internal standard is included in the various steps of the labeling assay and chromatographic separation. Thus, the internal standard provides a means by which variables, such as the efficiency of labeling and possible loss of product during chromatographic separation, can be taken into account in achieving an accurate quantitation of the thymine glycol DNA base modification by the method of the present invention. Further, a carrier (of a chemical structure illustrated in FIG. 4D) for the internal standard is synthesized from the internal standard by cold-phosphorylating the internal standard. Thus, using methods illustrated in Example 1 herein, polynucleotide kinase and ATP can be used to phosphorylate the internal standard in constructing a carrier for the internal standard, wherein the carrier is used to track and unequivocally locate (e.g., by natural fluorescence, or by ultraviolet absorption) the internal standard by co-migration with the internal standard during chromatographic separations.

In an additional aspect of this embodiment according to the present invention, provided is a kit for a method for detecting and quantitating the thymine glycol modification in a DNA sample, wherein the kit comprises components selected from the group consisting of a chemically synthesized carrier for the thymine glycol modification, an internal standard, a carrier for the internal standard, ancillary reagents used in the nuclease digestion step, ancillary reagents used in the labeling step, and a combination thereof.

Dihydrothymine

In one aspect of this embodiment, the DNA base modification to be detected and quantitated is dihydrothymine.

The dihydrothymine modification (d(T*pA)) is known to be type of DNA base damage produced by ionizing radiation under anoxic conditions. Using the methods essentially according to Example 1 herein and additional compositions as described herein, a method of detecting and quantitating the dihydrothymine modification in a sample of DNA comprises a nuclease digestion step, a labeling step, and a chromatographic separation step. First, the sample of DNA to be assayed is digested with endonuclease, and dephosphorylated with acid phosphatase. As shown in Table 1, the dihydrothymine DNA base modification prevents or significantly inhibits the hydrolysis of the neighboring phosphodiester bond by an endonuclease. Therefore, the bulk of the DNA digest is in the form of nucleoside monomers which are not acceptable substrates for the phosphorylation step, and the remainder is modified dinucleoside monophosphates containing the dihydrothymine modification which can be selectively labeled with a detectable label. The digested dephosphorylated DNA may then be chromatographed to separate the modified dinucleoside monophosphates containing the dihydrothymine modification from the nucleoside monomers. From this step on in the method, it may be desirable to include an internal standard for the dihydrothymine modification to assist in the accurate quantitation of the dihydrothymine modification present in the sample DNA. The modified dinucleoside monophosphates and a known amount of the internal standard are then enzymatically labeled with a detectable label in the same reaction mixture, and the labeled modified dinucleoside monophosphates and labeled internal standard (labeled products) are separated from the radioactive debris residual from labeling by a simple filtration procedure in reducing significantly the level of background radioactivity. To further purify the labeled products from background, the labeled products are subjected to chromatographic separation (e.g., TLC or HPLC). In preparing the labeled products for chromatography, a carrier for the dihydrothymine modification is added to track and unequivocally locate (e.g., by natural fluorescence, or by ultraviolet absorption) the labeled modified dinucleoside monophosphates comprising the dihydrothymine modification during the chromatographic separation; and a carrier for the internal standard is added to track and unequivocally locate the labeled internal standard during the chromatographic separation. The amount of label for the labeled modified dinucleoside monophosphates comprising the dihydrothymine modification, and the amount of label for the labeled internal standard can then be detected and measured. Using the known amount of the internal standard as a reference, the moles of the dihydrothymine modification can be quantitated from the measure of label. e.g.:

$$\frac{\text{amount of label (std.)}}{\text{known amount of std.}} = \frac{\text{amount of label (from DNA sample)}}{\text{amount of dihydrothymine in sample}}$$

As described previously, the internal standard is necessary for the quantitation of the DNA base modification because of such variables as the efficiency of phosphorylation.

Figure 5A:
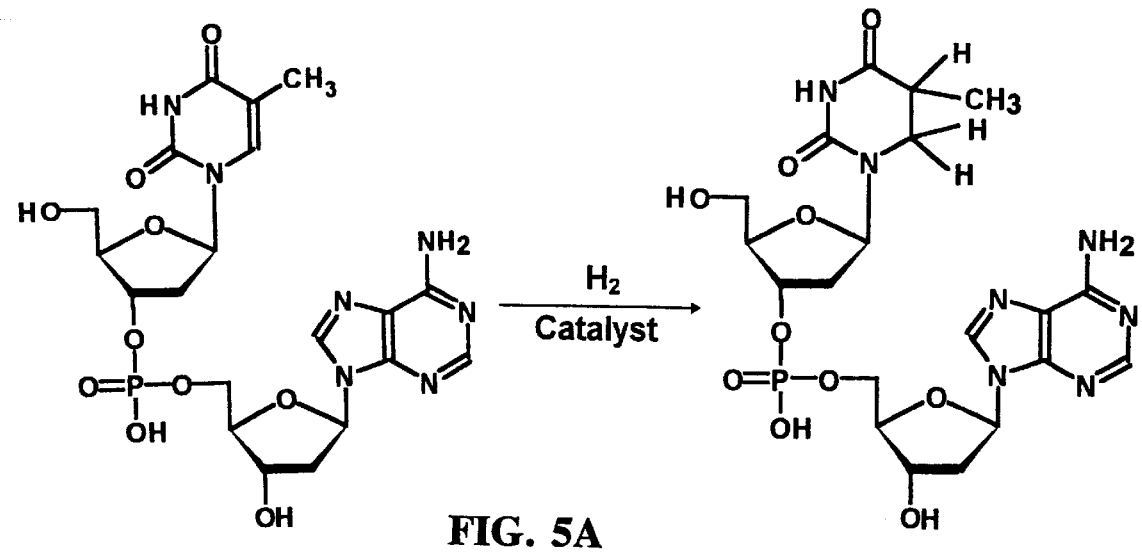
FIG. 5A illustrates a step in the chemical synthesis of the carrier shown in FIG. 5B.
Figure 5B:
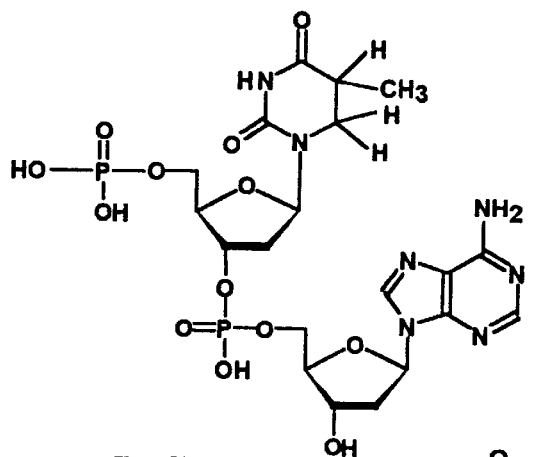
FIG. 5B is a chemical structure of a carrier for detecting and quantitating a dihydrothymine modification.
Figure 5C:
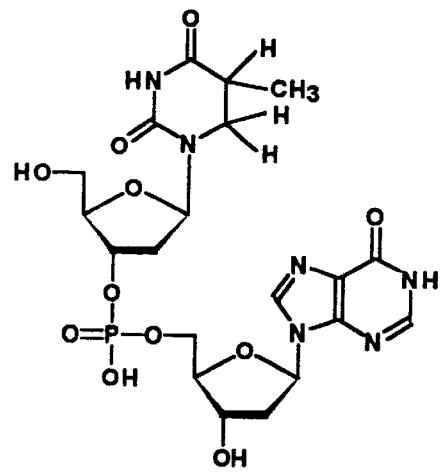
FIG. 5C is a chemical structure of a internal standard for detecting and quantitating a dihydrothymine modification.
Figure 5D:
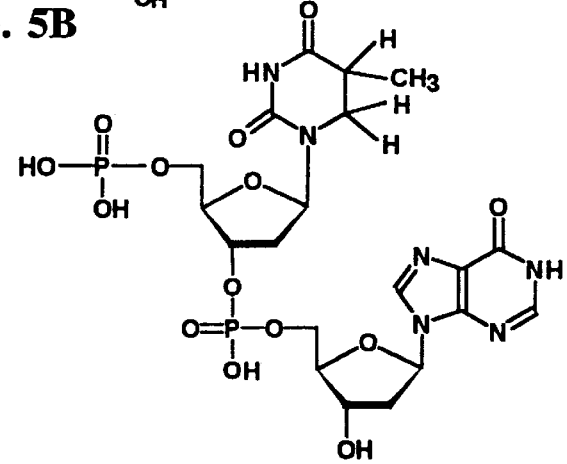
FIG. 5D is a chemical structure of a carrier for the internal standard shown in FIG. 5C.

In continuing with this aspect of the embodiment of the present invention, illustrated and provided are compositions for improving the efficiency and sensitivity of the method according to the present invention for detecting and quantitating the DNA base modification comprising the dihydrothymine modification. Also illustrated and provided in this embodiment are methods for reliably and efficiently producing the compositions according to the present invention. For the carrier for the dihydrothymine modification, the initial step involves the chemical synthesis of the dinucleoside monophosphate d(TpA) in bulk, as was described above and as illustrated in FIG. 2A. FIG. 5A summarizes the synthesis of the carrier for the dihydrothymine modification from d(TpA). The carrier for the dihydrothymine modification is synthesized from d(TpA) by dissolving 10 mg of d(TpA) in 10ml $H_2O$, and then adding 10 mg of rhodium-alumina catalyst. The mixture is hydrogenated with shaking for five hours at 3.3 atmospheres. Purification is accomplished by HPLC as described above. The carrier, the chemical structure as shown in FIG. 5B, is used for tracking and unequivocally locating in the method of the present invention for detecting and quantitating the DNA base modification comprising the dihydrothymine modification. Also in this embodiment, provided are an internal standard, and the carrier for the internal standard, for detecting and quantitating the DNA base modification comprising the dihydrothymine modification. For the internal standard and the carrier for the internal standard, the initial step in each synthetic procedure involves the chemical synthesis of the dinucleoside monophosphate d(TpI) in bulk, as described above and as illustrated in FIG. 3A. From the d(TpI) was synthesized an internal standard for the dihydrothymine modification. The internal standard was synthesized by incubating d(TpI) in the presence of a rhodiumalumina catalyst, with subsequent purification by chromatography as essentially described above for producing the carrier for the dihydrothymine modification. The internal standard, as illustrated in FIG. 5C, has a deoxyribose molecule to which a terminal phosphate group can be added at position 5'. In one aspect of this embodiment, the internal standard is labeled using a detectable label such as $\gamma^{32}P$, by using polynucleotide kinase and $\gamma^{32}P$-ATP. Thus, using methods illustrated in Example 1 herein, a known amount of the internal standard can be labeled in the same reaction in which the dihydrothymine modified dinucleoside monophosphate purified from the DNA digest is labeled. The internal standard is present in the various steps of the labeling assay and chromatographic separation. Thus, the internal standard provides a means by which variables, such as the efficiency of labeling and possible loss of product during chromatographic separation, can be taken into account in achieving an accurate quantitation of the dihydrothymine DNA base modification by the method of the present invention. Further, a carrier (of a chemical structure as illustrated in FIG. 5D) for the internal standard is synthesized from the internal standard by cold-phosphorylating the internal standard. Thus, using methods illustrated in Example 1 herein, polynucleotide kinase and ATP can be used to phosphorylate the internal standard in constructing a carrier for the internal standard, wherein the carrier is used to track and unequivocally locate (e.g., by natural fluorescence, or by ultraviolet absorption) the internal standard by co-migration with the internal standard during chromatographic separations.

In an additional aspect of this embodiment, according to the present invention, provided is a kit for a method for detecting and quantitating the dihydrothymine modification in a DNA sample, wherein the kit comprises components selected from the group consisting of a chemically synthesized carrier for the dihydrothymine modification, an internal standard, a carrier for the internal standard, ancillary reagents used in the nuclease digestion step, ancillary reagents used in the labeling step, and a combination thereof.

Formamido remnant (d(T*pG). d(T*pC), d(T*pA) or d(T*pT))

In one aspect of this embodiment, the DNA base modification to be detected and quantitated is formamido remnant having a modification of the 5' nucleoside consisting of either d(T*pG), d(T*pC), d(T*pA), or d(T*pT). The formamido remnant is generated by the action of a hydroxyl radical in the presence of oxygen. Using the methods essentially according to Example 1 herein, a method of detecting and quantitating a formamido remnant consisting of either d(T*pG), d(T*pC), d(T*pA) or d(T*pT) in a sample of DNA comprises a nuclease digestion step, a labeling step, and a chromatographic separation step. First, the sample of DNA to be assayed is digested with endonuclease, and dephosphorylated with acid phosphatase. As shown in Table 1, the formamido remnant consisting of either d(T*pG), d(T*pC), d(T*pA), or d(T*pT) prevents or significantly inhibits the hydrolysis of the neighboring phosphodiester bond by an endonuclease. Therefore, the bulk of the DNA digest is in the form of nucleoside monomers which are not acceptable substrates for the phosphorylation step, and the remainder is modified dinucleoside monophosphates containing this formamido remnant which can be selectively labeled with a detectable label. The digested dephosphorylated DNA may then be chromatographed to separate the modified dinucleoside monophosphates containing this formamido remnant from the nucleoside monomers. From this step on in the method, it may be desirable to include an internal standard for this formamido remnant to assist in the accurate detection and quantitation of this formamido remnant present in the sample DNA. The modified dinucleoside monophosphates and the internal standard are then enzymatically labeled with a detectable label in the same reaction mixture, and the labeled modified dinucleoside monophosphates and labeled internal standard (labeled products) are separated from the radioactive debris residual from labeling by a simple filtration procedure in reducing significantly the level of background radio-activity. To further purify the labeled products from background radio-activity, the labeled products are subjected to chromatographic separation (e.g., TLC or HPLC). In preparing the labeled products for chromatography, a carrier for this formamido remnant is added to track and unequivocally locate (e.g., by natural fluorescence, or by ultraviolet absorption) the labeled modified dinucleoside monophosphates comprising this formamido remnant during the chromatographic separation; and a carrier for the internal standard is added to track and unequivocally locate the labeled internal standard during the chromatographic separation. The amount of label for the labeled modified dinucleoside monophosphates comprising this formamido remnant, and the amount of label for the labeled internal standard can then be detected and measured. Using the internal standard as a reference, the moles of this formamido remnant can be quantitated from the measure of label. As described previously, the internal standard is necessary for the quantitation of the DNA base modification because of such variables as the efficiency of phosphorylation. Carriers, internal standards, and carriers for the internal standard, for the formamido remnant (consisting of either d(T*pG), d(T*pC), d(T*pA), or d(T*pT)) may be synthesized by one of ordinary skill in the art using the chemical principles set forth in Example 2 herein, and using the appropriate dimer (d(TpG), d(TpC), d(TpA), or d(TpT)) as a starting material.

In an additional aspect of this embodiment according to the present invention, provided is a kit for a method for detecting and quantitating the formamido remnant (consisting of either d(T*pG), d(T*pC), d(T*pA), or d(T*pT)) in a DNA sample, wherein the kit comprises components selected from the group consisting of a chemically synthesized carrier for the formamido remnant, an internal standard, a carrier for the internal standard, ancillary reagents used in the nuclease digestion step, ancillary reagents used in the labeling step, and a combination thereof.

EXAMPLE 5

In this embodiment of the present invention, illustrated and provided is a method comprising an endonucleasemediated partial hydrolysis step, a labeling step, and a chromatographic separation step to detect and quantitate a DNA base modification in a sample of DNA, wherein the DNA base modification retards, but does not significantly prevent hydrolysis of the phosphoester bond by an endonuclease, and wherein the DNA base modification is selected from the group consisting of 5-hydroxy-5-methylhydantoin, 5-hydroxymethyluracil, and 8-hydroxyguanine.

The obstacle to overcome when developing this method according to the present invention was whether a realistic quantitation of a DNA base modification could be obtained if such a modification conferred only partial resistance to endonuclease digestion. As will be apparent from the following description, such detection and quantitation may be performed using a partial endonuclease digestion. While the detection and quantitation of the 8-hydroxyguanine modification is exemplified in particular detail in the following illustrative embodiment, those skilled in the art will appreciate that the same principles of this method may be used to detect and quantitate 5-hydroxy-5-methylhydantoin, or 5-hydroxymethyluracil.

Turnover rates for each unmodified dinucleoside monophosphate was measured in a separate experiment, using methods provided in Example 3 herein, by quantitating the hydrolysis of the unmodified dinucleoside monophosphate by endonuclease as a function of time. It was observed that the amount of a particular dinucleotide monophosphate (dNpN') remaining in a DNA hydrosylate after partial digest by endonuclease partial digestion, and subsequent phosphatase treatment, is inversely proportional to the turnover rate (R) for that unmodified dinucleoside monophosphate:

$$\frac{[d(NpN')]}{[dN]} \sim \frac{1}{R_{NpN'}}$$

wherein the amount of DNA in the sample is represented by the amounts of nucleoside, dN.
This observation was extended to amount of a particular modified dinucleotide monophosphate (dN*pN') remaining in a DNA hydrosylate after partial digest by and endonuclease partial digestion and subsequent phosphatase treatment:

$$\frac{[d(N^*pN')]}{[dN^*]} \sim \frac{1}{R_{N^*N'}}$$

To test this observation, and for purposes of illustration, a DNA sample was exposed to 60 Gy of ionizing radiation to generate the radiation-induced DNA base modification 8-hydroxyguanine d(G*pT). The DNA base modification 8-hydroxyguanine d(G*pT) present in the DNA sample was detected and quantitated according to the methods illustrated in Examples 1 and 3 herein. The DNA sample was enzymatically digested in forming a DNA hydrosylate containing modified dinucleoside monophosphates and nucleoside monomers. The modified dinucleoside monophosphates and the internal standard were then enzymatically labeled with a detectable label in the same reaction mixture, and the labeled modified dinucleoside monophosphates and labeled internal standard (labeled products) were separated from the radioactive debris residual from labeling by a simple filtration procedure in reducing significantly the level of background radioactivity. To further purify the labeled products from background radioactivity, the labeled products are subjected to chromatographic separation (e.g., TLC or HPLC). In preparing the labeled products for chromatography, a carrier for the 8-hydroxyguanine was added to track and unequivocally locate (e.g., by natural fluorescence, or by ultraviolet absorption) the labeled modified dinucleoside monophosphates comprising the 8-hydroxyguanine during the chromatographic separation; and a carrier for the internal standard is added to track and unequivocally locate the labeled internal standard during the chromatographic separation. The amount of label for the labeled modified dinucleoside monophosphates comprising the 8-hydroxyguanine modification, and the amount of label for the labeled internal standard were then detected and measured. Using the method according to the present invention, the amount of 8-hydroxyguanine in the DNA sample was calculated to be 17.3 pm/$\mu$g. This measurement correlated with the amount 15.5 pm/$\mu$g of 8-hydroxyguanine in the same DNA sample which was measured by an independent method. Thus, using the method according to the present invention, quantitation of a DNA base modification may be obtained for modifications that confer only partial resistance to endonuclease digestion. Such a DNA base modification is selected from the group consisting of 5-hydroxy-5-methylhydantoin, 5-hydroxymethyluracil, and 8-hydroxyguanine.

In an additional aspect of this embodiment according to the present invention, provided is a kit for a method for detecting and quantitating in a DNA sample a DNA base modification selected from the group consisting of 5-hydroxy-5-methylhydantoin, 5-hydroxymethyluracil, or 8-hydroxyguanine, wherein the kit comprises components selected from the group consisting of a chemically synthesized carrier for the DNA base modification, an internal standard for the DNA base modification, a carrier for the internal standard, ancillary reagents used in the nuclease digestion step, ancillary reagents used in the labeling step, and a combination thereof.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept. For example, by using the teachings of the present invention those skilled in the art of chemistry may synthesize other carriers, internal standards, and carriers for internal standards, or modify the illustrative compositions described herein, which could then be used with the method of the present invention. Such modifications and/or adaptations are intended to be within the meaning and scope of the appended claims.

We claim:

1. A method for detecting and quantitating a DNA base modification in a sample of DNA, wherein the DNA base modification is selected from the group consisting of thymine glycol, dihydrothymine, a tandem base modification d(T*pG*), and a formamido remnant comprising d(T*pG) or d(T*pC) or d(T*pT) or d(T*pA), wherein * represents a modification of the base, comprising:

(a) contacting the sample with an endonuclease and allowing the endonuclease to digest the DNA, wherein the digested DNA comprises modified dinucleoside monophosphates comprising the DNA base modification, and nucleoside monomers;

(b) dephosphorylating the digested DNA;

(c) adding to the dephosphorylated digested DNA a known amount of an internal standard, wherein the internal standard is detectably labeled to standardize the efficiency of phosphorylation of the dinucleoside monophosphate;

(d) labeling the dephosphorylated digested DNA and the internal standard with a detectable label forming labeled products;

(e) adding to the labeled products, a carrier molecule which chromatographically co-migrates with the modified dinucleoside monophosphates present in the labeled products, and an internal standard carrier molecule which chromatographically co-migrates with the internal standard;

(f) chromatographically separating labeled modified dinucleoside monophosphates and the carrier molecule together, and chromatographically separating labeled internal standard and the internal standard carrier molecule together; and (g) measuring the amount of detectable label in the labeled modified dinucleoside monophosphates of step (f), and measuring the amount of detectable label in the labeled internal standard of step (f);

wherein the amount of the DNA base modification in the sample DNA is quantitated by comparing the known amount of the internal standard relative to the amount of detectable label measured in the internal standard, to the amount of detectable label measured in the labeled modified dinucleoside monophosphates.

2. The method according to claim 1, wherein the DNA base modification detected and quantitated is dihydrothymine.

3. The method according to claim 2, wherein the carrier molecule which chromatographically co-migrates with the DNA base modification is a molecule having the chemical structure shown in FIG. 5B, wherein the internal standard is a molecule having the chemical structure shown in FIG. 5C, and wherein the internal standard carrier molecule which chromatographically co-migrates with the internal standard is a molecule having the chemical structure shown in FIG. 5D.

4. The method according to claim 1, wherein the DNA base modification detected and quantitated is the formamido remnant.

5. The method according to claim 4, wherein the carrier molecule which chromatographically co-migrates with the DNA base modification is a molecule having the chemical structure shown in FIG. 2B, wherein the internal standard is a molecule having the chemical structure shown in FIG. 3B, and wherein the internal standard carrier molecule which chromatographically co-migrates with the internal standard is a molecule having the chemical structure shown in FIG. 3C.

6. The method according to claim 1, wherein the DNA base modification detected and quantitated is thymine glycol.

7. The method according to claim 6, wherein the carrier molecule which chromatographically co-migrates with the DNA base modification is a molecule having the chemical structure shown in FIG. 4B, wherein the internal standard is a molecule having the chemical structure shown in FIG. 4C, and wherein the internal standard carrier molecule which chromatographically co-migrates with the internal standard is a molecule having the chemical structure shown in FIG. 4D.

8. A method for producing a carrier molecule, wherein the carrier molecule has the chemical structure shown in FIG. 2B, said method comprising mixing dinucleoside monophosphate d(TpA) with ascorbic acid in a nitrogen-saturated buffer, purging the mixture with oxygen, isolating dinucleoside monophosphate d(T*pA) formed by chromatography, and phosphorylating the dinucleoside monophosphate d(T*pA), wherein * represents a modification according to the chemical structure shown in FIG. 2B.

9. A method for producing a dinucleoside monophosphate d(TpI) comprising synthesizing a condensation product from 5'-O-dimethyoxytrityl-thymidine-3'-(o-chlorophenyl) phosphate barium salt and 2'-deoxyinosine using a phosphotriester method, removing base labile protecting groups from the condensation product by treating the condensation product with a strong base, removing acid labile protecting groups from the condensation product by treating the condensation product with an acid, and purifying the dinucleoside monophosphate by chromatographic separation.

10. A method for producing an internal standard, wherein the internal standard has the chemical structure shown in FIG. 3B, said method comprising mixing dinucleoside monophosphate d(TpI) with ascorbic acid in a nitrogen-saturated buffer, purging the mixture with oxygen, and isolating dinucleoside monophosphate d(T*pI) by chromatography, wherein * represents a modification according to the chemical structure shown in FIG. 3B.

11. A method for producing an internal standard carrier, wherein the internal standard carrier has the chemical structure shown in FIG. 3C, said method comprising mixing dinucleoside monophosphate d(TpI) with ascorbic acid in a nitrogen-saturated buffer, purging the mixture with oxygen, isolating dinucleoside monophosphate d(T*pI) by chromatography, and phosphorylating the dinucleoside monophosphate d(T*pI) with non radioactive phosphorous, wherein * represents a modification according to the chemical structure shown in FIG. 3C.

12. A kit for a method for detecting and quantitating a DNA base modification comprising formamido remnant in a DNA sample, wherein the method comprises quantitating dinucleoside monophosphates comprising formamido remnant, wherein the kit comprises:

a carrier for the dinucleoside monophosphate comprising formamido remnant, wherein the carrier for the dinucleoside monophosphate comprising formamido remnant chromatographically comigrates with the dinucleoside monophosphate comprising formamido remnant;

an internal standard, wherein the internal standard is detectably labeled to standardize the efficiency of phosphorylation of the dinucleoside monophosphate; and an internal standard carrier, wherein the internal standard carrier molecule chromatographically comigrates with the internal standard, wherein the carrier for the dinucleoside monophosphate comprising formamido remnant, the internal standard, and the internal standard carrier are different molecules, and wherein the internal standard has a 5' dephosphorylated deoxyribose.

13. The kit according to claim 12, wherein the carrier for the dinucleoside monophosphate comprising the formamido remnant has a chemical structure shown in FIG. 2B, wherein the internal standard has a chemical structure shown in FIG. 3B, and wherein the internal standard carrier has a chemical structure shown in FIG. 3C.

14. The kit according to claim 12 further comprising components selected from the group consisting of reagents used in an endonuclease digestion step, reagents used in a labeling step, and a combination thereof.

15. A method for producing an internal standard, wherein the internal standard has the chemical structure shown in FIG. 4C, said method comprising mixing dinucleoside monophosphate d(TpI) with $OsO_4$, and isolating dinucleoside monophosphate d(T*pI) by chromatography, wherein * represents a modification according to the chemical structure shown in FIG. 4C.

16. A method for producing an internal standard carrier, wherein the internal standard carrier is a molecule having the chemical structure shown in FIG. 4D, said method comprising mixing dinucleoside monophosphate d(TpI) with $OsO_4$, isolating dinucleoside monophosphate d(T*pI) by chromatography, and phosphorylating the dinucleoside monophosphate d(T*pI) with nonradioactive phosphorous, wherein * represents a modification according to the chemical structure shown in FIG. 4D.

17. A kit for a method for detecting and quantitating a DNA base modification comprising thymine glycol in a DNA sample, wherein the method comprises quantitating dinucleoside monophosphates comprising thymine glycol, wherein the kit comprises:

a carrier for the dinucleoside monophosphate comprising thymine glycol, wherein the carrier for the dinucleoside monophosphate comprising thymine glycol chromatographically comigrates with the dinucleoside monophosphate comprising thymine glycol;

an internal standard, wherein the internal standard is detectably labeled to standardize the efficiency of phosphorylation of the dinucleoside monophosphate; and an internal standard carrier, wherein the internal standard carrier molecule chromatographically comigrates with the internal standard, wherein the carrier for the dinucleoside monophosphate comprising thymine glycol, the internal standard, and the internal standard carrier are different molecules, and wherein the internal standard has a 5' dephosphorylated deoxyribose.

18. The kit according to claim 17, wherein the carrier for the dinucleoside monophosphate comprising the thymine glycol has a chemical structure shown in FIG. 4B, wherein the internal standard has a chemical structure shown in FIG. 4C, and wherein the internal standard carrier has a chemical structure shown in FIG. 4D.

19. The kit according to claim 17 further comprising components selected from the group consisting of reagents used in an endonuclease digestion step, reagents used in a labeling step, and a combination thereof.

20. A method for producing an internal standard, wherein the internal standard has the chemical structure shown in FIG. 5C, said method comprising mixing dinucleoside monophosphate d(TpI) with a rhodium-alumina catalyst, hydrogenating the mixture, and isolating dinucleoside monophosphate d(T*pI) by chromatography, wherein * represents a modification according to the chemical structure shown in FIG. 5C.

21. A method for producing an internal standard carrier, wherein the internal standard carrier is a molecule having the chemical structure shown in FIG. 5D, said method comprising mixing dinucleoside monophosphate d(TpI) with a rhodium-alumina catalyst, hydrogenating the mixture, isolating dinucleoside monophosphate d(T*pI) by chromatography, and phosphorylating the dinucleoside monophosphate d((T*pI) with nonradioactive phosphorous, wherein * represents a modification according to the chemical structure shown in FIG. 5D.

22. A kit for a method for detecting and quantitating a DNA base modification comprising dihydrothymine in a DNA sample, wherein the method comprises quantitating dinucleoside monophosphates comprising dihydrothymine, wherein the kit comprises:

- a carrier for the dinucleoside monophosphate comprising dihydrothymine, wherein the carrier for the dinucleoside monophosphate comprising dihydrothymine chromatographically comigrates with the dinucleoside monophosphate comprising dihydrothymine;
- an internal standard, wherein the internal standard is detectably labeled to standardize the efficiency of phosphorylation of the dinucleoside monophosphate; and
- an internal standard carrier, wherein the internal standard carrier molecule chromatographically comigrates with the internal standard,
- wherein the carrier for the dinucleoside monophosphate comprising dihydrothymine, the internal standard, and the internal standard carrier are different molecules, and wherein the internal standard has a 5' dephosphorylated deoxyribose.

23. The kit according to claim 22, wherein the carrier for the dinucleoside monophosphate comprising the dihydrothymine has a chemical structure shown in FIG. 5B, wherein the internal standard has a chemical structure shown in FIG. 5C, and wherein the internal standard carrier has a chemical structure shown in FIG. 5D.

24. The kit according to claim 22 further comprising components selected from the group consisting of reagents used in an endonuclease digestion step, reagents used in a labeling step, and a combination thereof.

25. A method for detecting and quantitating a DNA base modification in a sample of DNA, wherein the DNA base modification is selected from the group consisting of 5-hydroxy-5-methylhydantoin, 5-hydroxymethyluracil, and 8-hydroxyguanine, comprising:

(a) contacting the DNA sample with an endonuclease and allowing the endonuclease to partially digest the DNA, wherein the partially digested DNA comprises modified dinucleoside monophosphates comprising the DNA base modification, and nucleoside monomers;

(b) dephosphorylating the partially digested DNA;

(c) adding to the dephosphorylated partially digested DNA a known amount of an internal standard;

(d) labeling the dephosphorylated partially digested DNA and the internal standard with a detectable label forming labeled products;

(e) adding to the labeled products, a carrier molecule which chromatographically co-migrates with the modified dinucleoside monophosphates present in the labeled products, and an internal standard carrier molecule which chromatographically co-migrates with the internal standard;

(f) chromatographically separating labeled modified dinucleoside monophosphates and the carrier molecule together, and chromatographically separating labeled internal standard and the internal standard carrier molecule together; and (g) measuring the amount of detectable label in the labeled modified dinucleoside monophosphates of step (f), and measuring the amount of detectable label in the labeled internal standard of step (f);

wherein the amount of the DNA base modification in the sample DNA is quantitated by comparing the known amount of the internal standard relative to the amount of detectable label measured in the internal standard, to the amount of detectable label measured in the labeled modified dinucleoside monophosphates.

26. The method according to claim 25, wherein the DNA base modification detected and quantitated is 5-hydroxy-5-methylhydantoin.

27. The method according to claim 25, wherein the DNA base modification detected and quantitated is 5-hydroxymethyluracil.

28. The method according to claim 25, wherein the DNA base modification detected and quantitated is 8-hydroxyguanine.

29. A kit for a method for detecting and quantitating in a DNA sample a DNA modification selected from the group consisting of 5-hydroxy-5-methylhydantoin, 5-hydroxymethyluracil, and 8-hydroxyguanine, wherein the method comprises quantitating dinucleoside monophosphates comprising the DNA base modification, wherein the kit comprises:

- a chemically synthesized carrier for the dinucleoside monophosphate comprising the DNA base modification, wherein the carrier for the dinucleoside monophosphate comprising the DNA base modification chromatographically comigrates with the dinucleoside monophosphate comprising the DNA base modification;
- an internal standard for the DNA base modification, wherein the internal standard is detectably labeled to standardize the efficiency of phosphorylation of the dinucleoside monophosphate; and
- an internal standard carrier, wherein the internal standard carrier molecule chromatographically comigrates with the internal standard.

30. The kit according to claim 29 further comprising components selected from the group consisting of reagents used in an endonuclease digestion step, reagents used in a labeling step, filters for the labeling step, and a combination thereof.

* * * * *

UNITED STATES PATENT AND TRADEMARK OFFICE
CERTIFICATE OF CORRECTION

PATENT NO. : 5,906,918
DATED : May 25, 1999
INVENTOR(S) : Harold C. Box; Alexander E. Maccubbin; Edwin E. Budzinski; Herbert Iijima It is certified that error appears in the above-identified patent and that said Letters Patent is hereby corrected as shown below:

Col. 20, line 57, change "FIG. SC" to --FIG. 5C--

Signed and Sealed this

Sixteenth Day of November, 1999

Attest:

Q. TODD DICKINSON

*Attesting Officer*   *Acting Commissioner of Patents and Trademarks*